United States Patent
Dütting et al.

[11] Patent Number: 5,989,181
[45] Date of Patent: Nov. 23, 1999

[54] DEVICE FOR ENDOSCOPIC DIAGNOSIS AND TREATMENT OF TISSUE

[75] Inventors: Kaspar Dütting, Stuttgart; Marc Schurr, Tübingen; Gerhard Buess, Tübingen-Bebenhausen; Gerhard Müller, Berlin; Bernd Wagner, Looft, all of Germany

[73] Assignee: Richard Wolf GmbH, Knittlingen, Germany

[21] Appl. No.: 08/968,047

[22] Filed: Nov. 10, 1997

[30] Foreign Application Priority Data

Nov. 8, 1996 [DE] Germany ............... 196 46 236

[51] Int. Cl.⁶ ........................................ A61B 1/04
[52] U.S. Cl. ............................ 600/108; 606/15
[58] Field of Search .................. 600/108; 606/2, 606/3, 14, 15, 16, 17; 607/89, 92, 93

[56] References Cited

U.S. PATENT DOCUMENTS 4,582,405  4/1986  Müller et al. .
4,974,076  11/1990  Nakamura .
5,309,895  5/1994  Yabe .
5,335,662  8/1994  Kimura et al. .
5,413,108  5/1995  Alfano .

FOREIGN PATENT DOCUMENTS 21 25 986  3/1984  United Kingdom .

OTHER PUBLICATIONS

Artile entitled "Programm im Rahmen des Zukunftskonzeptes Informationstechnik" from Mikrosystemtechnik 1994–1999, pp. 74–100.

Primary Examiner—John P. Leubecker
Attorney, Agent, or Firm—Cohen, Pontani, Lieberman & Pavane

[57] ABSTRACT

The device comprises a treatment laser and at least two diagnosis lasers of differing wavelengths, wherein a receiving means is allocated to each diagnosis laser. The signal of the receiving means is led to an electronic evaluation and control means. In the distal end section of the endosopic part of the device the light beams of all lasers are guided together.

15 Claims, 4 Drawing Sheets

DEVICE FOR ENDOSCOPIC DIAGNOSIS AND TREATMENT OF TISSUE

BACKGROUND OF THE INVENTION

1. Field of the Invention

The invention relates to a device for the endoscopic diagnosis and treatment of tissue in humans or animals using a laser.

2. Description of the Prior Art

Endoscopic devices of the previously mentioned type - such a device is known for example from U.S. Pat. No. 5,413,108- are used these days, for example, in rectoscopy. With such a device a slim distal end section of a generally flexible endoscope is introduced into the body via a body opening and is guided up to the location to be diagnosed or to be treated. The tissue region to be diagnosed, for example the wall of the colon, is irradiated by at least two diagnosis lasers of a different wavelength, after which the remitted light, be it either by reflection or by fluorescence, is acquired dependent on wavelength. The receiving signals are linked in a picture element dependent manner by way of subtraction or forming quotients, by which means the topology of the tissue section to be diagnosed is removed, thus by way of these electronic signal linkings, differences in intensity of the received picture, as for example arises with shadows, increases, deepenings and likewise, are removed. The remaining picture or electrical signal permits the desired diagnosis, by way of the wavelength dependent remission appearances of healthy and malignant tissue. After the diagnosis has been effected, the malignant tissue may be directly cauterized by the treatment laser, thus it can be removed. By way of the diagnosis laser directly afterwards, a control may be effected as to whether the malignant tissue has been completely removed or not.

The construction of the device of this known arrangement from U.S. Pat. No. 5,413,108 is such that the diagnosis laser as well as the treatment laser and the receiving means lie outside the endoscope and are connected to the distal endoscope end via an optic fiber. The wavelength separation is effected via filters which lie in a disk which engages in the beam path and can be driven by motor.

A similar arrangement is known from British reference GB 2125986 A. With this device the treatment laser is not led through a separate working channel, but is already integrated.

The disadvantages with the previously mentioned device is in particular the complicated and technically expensive construction. The light emitted by reflection or fluorescence is extremely weak and must be amplified in a technically expensive manner, before it can be received and evaluated. This finally leads to the fact that the diagnosis means has a relatively low sensitivity but also however does not function with the required reliability. Furthermore, with the prior known devices there often arises with the diagnosis, as well as with the therapy, problems with regard to the accuracy of the diagnosis location or therapy location.

BRIEF SUMMARY OF THE INVENTION

Proceeding from this state of the art it is the object of the invention to improve a device of the known type which on the one hand achieves has a high accuracy or sensitivity, but on the other hand has a less expensive and more robust construction.

Pursuant to this object, and others which will become apparent hereafter, one aspect of the present invention resides in a device for the endoscopic diagnosis and treatment of tissue with a treatment laser, which device includes at least one diagnosis laser for producing light beams of different wavelengths. At least one receiving means is provided for receiving the diagnosis light. Control and evaluation means are also provided. The device has a slim distal end section from which the light beams exit and the light guided to the receiving means enters. The receiving means are arranged in the distal end section of the endoscopic part of the device. Due to this construction the light emitted by fluorescence or reflection may be guided to the receiving means by the shortest path, avoiding complicated optical devices, so that the otherwise customary amplifier may be done away with. The guiding of the light within the distal end section, from the light entry to the receiving means, may as a rule be exclusively effected via mirrors so that a large part of this light may be guided to the receiving means or to the several receiving means. With this it is particularly essential that the application of the otherwise customary light guides in the region between light entry and receiving means may be completely done away with, by which means the otherwise conventional small acceptance angle may be considerably increased and thus the coupling losses may be very considerably reduced. The device according to the invention thus already conditioned by design, has a considerably higher sensitivity than that which is known from the state of the art, wherein the construction is already made considerably less expensive and simpler by the fact that the otherwise customary light amplifier may be completely done away with.

The accuracy with respect to the diagnosis and therapy location, according to a further embodiment of the invention, may further be increased by the beam paths of the emitted and incident light at the distal end of the device, i.e. the beam paths also from the diagnosis and treatment lasers, being brought to coincide.

The guiding together of the beam paths further also has design advantages and permits a slim formation of the device particularly in the end region.

As a rule, the device according to the invention may be operated with a diagnosis laser and a receiving means when the diagnosis laser as well as the receiving means are applied in a phased manner so that for a given time interval, light of a first wavelength is produced and received, and for a second interval light of a second wavelength is produced and received, as for example is described in U.S. Pat. No. 5,413,108. This however in extreme cases may lead to movement blurs, which is why in another embodiment of the invention at least two diagnosis lasers of differing wavelengths are provided. A receiving means arranged in the distal end section of the device is allocated to each diagnosis laser. Then both diagnosis lasers may be simultaneously operated. Correspondingly, the reception is effected so that with the electronic signal linking for eliminating topology, continuously, an almost real-time picture arises.

For many applications, the evaluation by way of heavily differing absorption/remission of the two diagnosis wavelength regions is advantageous. Here for removing the topology of the irradiated tissue region as a rule the irradiation with different wavelengths and a corresponding evaluation is sufficient. In some applications however it is also advantageous to provide three diagnosis lasers of different wavelengths which preferably cover the wavelength regions red, green and blue. Then it is the case that with the receiving signals obtained from the remitted light, in these three wavelength regions, additionally a natural color picture may be represented on a monitor. The treating surgeon may thus apart from the diagnosis picture formed numerically by subtraction, forming quotients or other suitable maser, employ his experience collected from the natural observation picture.

In order to obtain an exact high resolution diagnosis picture it is useful to let the diagnosis laser beams pass over the diagnosis field according to the manner of the Flying Spot method, in whose middle point the beam path of the therapy laser opens. In order to achieve inventive device advantageously comprises scanning means which are within the distal end section and which horizontally as well as vertically deflect the laser beams of the diagnosis laser before impinging. The respective deflection is electronically acquired so that diagnosis points determined dependent on time may be allocated to the field of diagnosis. Correspondingly the signals of the receiving means are linked so that there arises a picture indicating point matrix which by way of frequent enquiry, for example three times per second, may be supplied as a picture to a monitor which irrespective of the enquiry frequency may be cycled for example with 50 or 100 Hz for obtaining a steady picture. Such microscanners are known per Se. In this context "Microsystem technology 1994 to 1999, program in the framework of the future concept of information technology" (translation of title) published by the German Federal Ministry for Development and Technology - public work from January 1994 (ISBN 3-88135-276-7) is referred to, in particular to page 81. With this it is the case of semiconductor mirrors which are arranged in the manner of a seesaw and which comprise electrodes on the underside so that by way of electromagnetic impinging a seesaw motion is effected in the one or the other directions. These mirrors in the usual manner are operated in the region of resonance so that the evaluation electronics are merely to be adapted to the frequency of resonance. Furthermore it is also possible to move these mirrors in a directed manner by way of a directed electromagnetic impingement of the one or the other side in order to achieve the desired scanning effect, i.e. to influence, in a directed manner, the impinging point of a diagnosis laser beam in the field of diagnosis.

For a location accurate diagnosis it is however also advantageous to have a receiving means allocated to each diagnosis laser, the receiving means being selectively provided only for receiving the light in the wavelength which is emitted by the laser. A particularly good arrangement for achieving an intensive and well detectable signal results when the receiving means are arranged within the distal end section, and this being between the distal end of the device and the scanning means. Then the reception may be effected with conventional photodiodes (comparatively large surfaced) since as a receiving signal all of the light of the respective diagnosis laser remitted by the tissue is always available. The evaluation as a picture element matrix is effected according to the temporal allocation of the individual picture elements.

In still a further embodiment, when a photodiode is allocated to each receiving means wherein the wavelength dependent division of the remitted light may be effected in a manner known per se via semi-permeable, dicroitically coated prisms or prism arrangements. Advantageously, the evaluation of the receiving signals is linked to release or activation control of the treatment laser so that, for example, an activation of the treatment laser is only possible when a predetermined threshold value (characterizing malignant tissue) within the picture region encompassing the treatment laser is exceeded. On the other hand an active engaging in the control of the treatment laser may be effected in a manner such that an automatic activation is effected upon exceeding a predetermined threshold value.

For the practical use of the device it is particularly useful to provide an auto-focusing means, which is known per se. This auto-focusing means may be integrated into the distal end section, to a large extent using available components, even when the beam path thereof coincides with that of the diagnosis laser as well as that of the treatment laser in the distal end of the device. Preferably the focusing lens of the auto-focusing means in the distal end section is arranged directly in front of a distal closing window and for the purpose of focusing is displaceable in the axial direction of the beam path by way, for example, of a usual magnet coil arrangement by way of electromagnetic impinging.

Preferably the auto-focusing means works with the wavelength region remitted most insensitively (lowest absorption e.g. 1.3 km in the infrared region and 0.35 gm in the UV region) whereby for this the light emitted from the corresponding diagnosis laser may be used when a corresponding temporal cycling between the reception required for the auto-focusing means and the reception required for the diagnosis is effected. In this case the photodiodes of the receiving means may also form part of the auto-focusing means. This not only leads to an inexpensive and space saving design of the endoscopic end section, but also to a particularly high accuracy of the auto-focusing means and thus to a high target accuracy of the whole device.

BRIEF DESCRIPTION OF THE DRAWINGS

The invention is hereinafter described in more detail by way of embodiment examples shown in the drawings. There are shown.

DETAILED DESCRIPTION OF THE INVENTION

Figure 2:
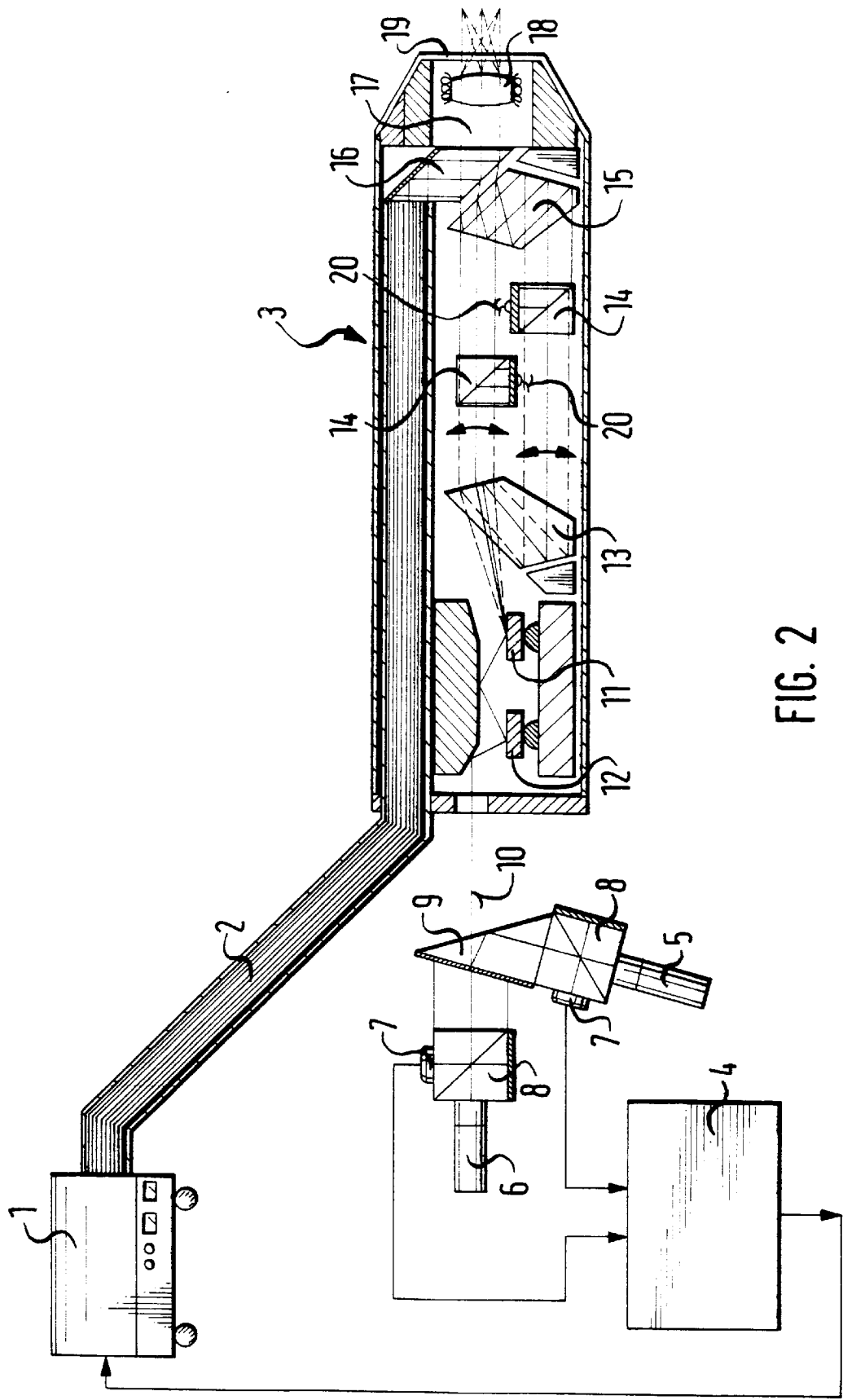
FIG. 2 in a heavily simplified schematic representation, the device according to the invention with a distal end section shown in longitudinal section.

The device according to FIG. 2 comprises a treatment laser 1. In this embodiment it is a Nd-YAG-laser functioning in the 1.06~tm region. The light of the treatment laser 1 is guided via a multimode fibre bundle 2 which opens in a distal end section 3 of an endoscopic instrument which here is not represented nor described in detail, for example of a flexible endoscope similar to that known from U.S. Pat. No. 5,413,108. Outside of the endoscopic instrument there is furthermore arranged an electronic evaluation, control unit 4 as well as two diagnosis lasers 5, 6. Each diagnosis laser 5, 6 is connected to a receiving means for remitted light in the form of a photodiode 7 via a beam splitter block constructed from two prisms. The diagnosis lasers 5, 6 with the allocated photodiodes 7 are again linked via a common part-mirrored prism 9 into the same beam path of a monomode fiber 10 which likewise opens into the distal end section 3. The diagnosis lasers 5, 6 function with this embodiment in a wavelength region of 1.31~m or 1.55~m these comprise an absorption differing up to the factor 10 and thus remission in the tissue. Similar differences may be achieved in the UV region (0.2~m and 0.35~m wavelength). The lasers 5, 6 are formed as laser diodes wherein the laser 5 working in the 1.31 rim-region serves essentially for acquiring the topology of the tissue region to be examined whereas the laser 6 working in the 1.55 km-region serves for acquring the topology and tissue-specific observations.

The laser beams of the diagnosis lasers 5, 6 which reach into the distal end section 3 via the monomode fiber 10 are firstly led within the end section 3 to a vertical scanner 12 and subsequently to a horizontal scanner 11 via suitable mirror arrangements. The scanners 11, 12 are silicon two-axis scanners which, due to electromagnetic stimulation in a predetermied frequency, oscillate about an axis. The axes of the scanners 11, 12 are arranged such that the light beams coming from the monomode fiber 10 are deflected into two planes displaced at 900 to one another. Due to this deflection, point-shaped light beams are directed onto an essentially quadratic field. Since the oscillation of the scanners 11, 12 is effected by electromagnetic stimulation and the oscillation frequency is known, a temporal allocation of the scanners may be effected, so that within the electrical control unit 4 it may be allocated to which point of the previously mentioned, approximately quadratic field the light beams are momentarily directed.

From the scanners 11, 12 the light beams of the diagnosis lasers 5, 6 are led via a prism block 13, in each case dependent on wavelength, to a beam splitter block 14 in order then in a further distally arranged prism block 15 to be reunified. Via a further prism block 16 lying distally behind the prism block 15, the beam path of the treatment laser 1 is then coupled into this beam path of the diagnosis lasers 5, 6. A lens 18 of an auto-focusing means runs through this common beam path 17 before the beam path leaves the distal end section 3 of the device via the distal side window 19. The lens 18 is movable in the axial direction of the beam path 17 via a magnet-coil arrangement, as is conventional with auto-focusing means.

The light of the diagnosis lasers 5, 6 leaving the window 19 and which by way of the scanners 11, 12 brushes over a diagnosis field, is remitted by the tissue to be examined, in particular tissue reaches through the window 19, the lens 18, the prism block 16 to the prism block 15 where a wavelength dependent splitting is effected. Via the beam splitter blocks 14 the remitted light is then led to photodiodes 20 in a wavelength dependent manner, these also being part of the auto-focusing means. The auto-focusing means works in time windows in which the diagnosis and therapy function is interrupted while using the light from the diagnosis lasers 5, 6 reflected on the object. By displacing the lens 18 with the help of the photodiodes 20 the intensity maximum of the remitted light and thus the optimum focusing position of the lens 18 is determined.

Outside of this time window the light produced by the diagnosis lasers 5, 6 and remitted from the object reaches through the beam splitter blocks 14 via the prism block 13 to the scanners 11, 12 which throw this light via the prism 9 back to the beam splitter blocks 8, where by way of the photodiode 7 it is acquired with respect to its intensity. The signal of the photodiodes 7 is fed to the electrical evaluation and control unit 4, in which a picture element allocation corresponding to the momentary scanner position in the field of diagnosis, and thus the construction of a matrix consisting of picture elements is effected, this being wavelength dependent on the one hand for the remitted light from the diagnosis laser and on the other hand for the remitted light from the diagnosis laser 6.

Figure 1:
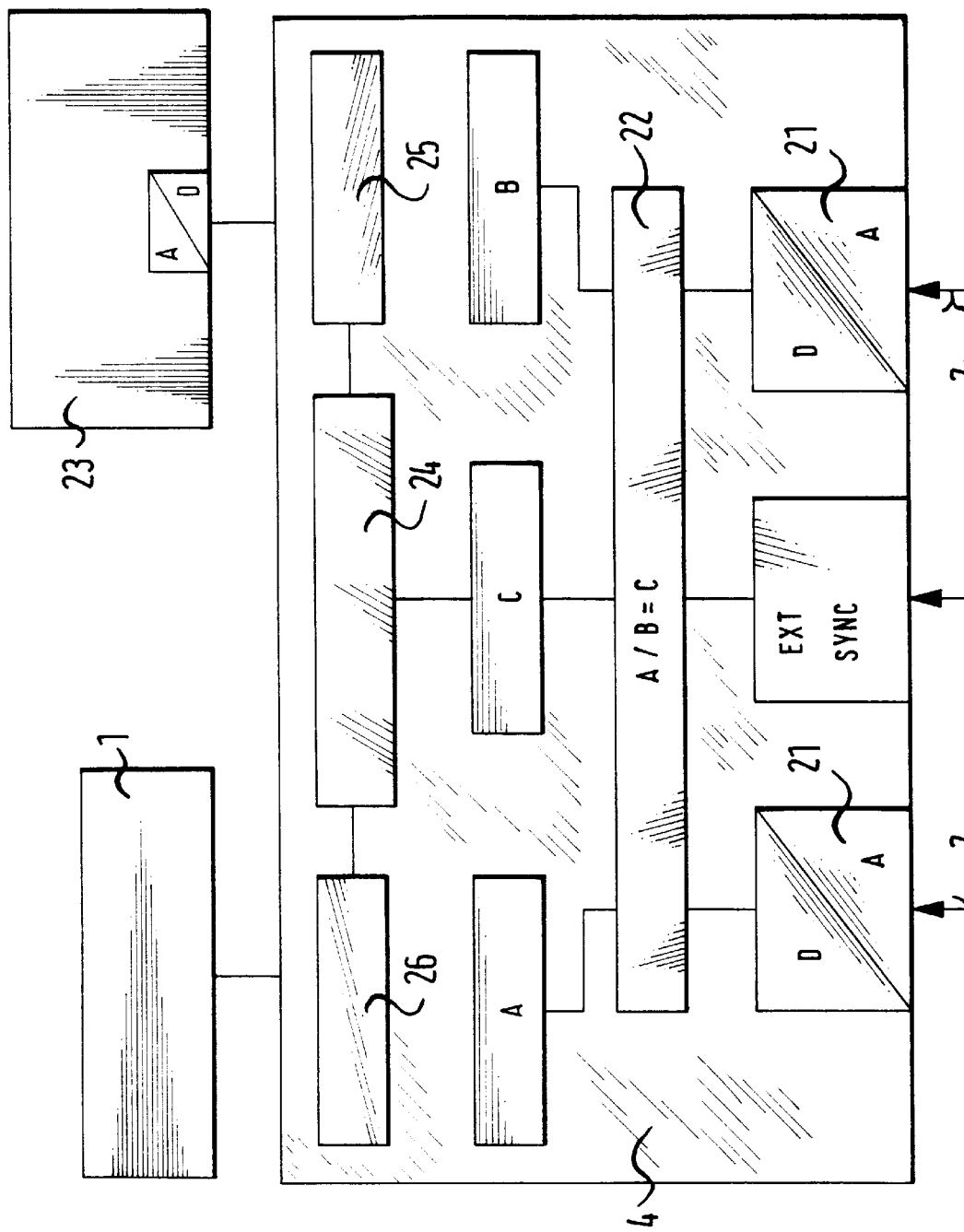
FIG. 1 is a simplified block diagram of the device according to the invention.

The signal processing within the control unit 4 is explained by way of the block diagram shown in FIG. 1. The signal of the photodiodes 7 is in each case firstly led to an analog to digital converter 21. The digital output signal of this analog to digital converter 21 is led to a central picture computer unit 22. In this picture computer unit 22 the data digitalized by the photodiodes 7 is processed in a wavelength dependent manner, with the help of the synchronization data of the scanners 11, 12, into picture matrix which is made up of individual picture elements and which in as far as it originates from remitted light of the diagnosis laser 5 is led to a picture memory A, and in as far as it originates film the remitted light of the diagnosis laser 6 is led to a picture memory B.

Furthermore, in the central picture computer unit 22 the wavelength dependent picture data is numerically linked, this being selectively by subtraction or by forming quotients. The picture which is numerically evaluated therefrom is led to a picture memory C. Since the picture memories A and B serve essentially for the accessing of the central picture computer unit 22 for determining the values for the picture memory C and can only selectively be represented on a monitor 23, in the picture memory C at regular intervals, for example three times per second, an analysis unit 24 is required. The looped through signal is processed in a video unit 25 and is represented on the monitor 23. On the monitor 23 thus the numerically linked picture of the picture memory C is represented. This picture, cleared of topology, thus only shows a picture from which the contours between malignant and healthy tissue may be recognized. By selectively switching on the pictures A and B, if desired, one may represent the topology alone or in addition.

Within the analysis unit 24 an electronic evaluation of the picture C is effected, in particular in the central region which is just covered by the treatment laser 1. Depending on a predetermined threshold value which may be preset, a signal is given to the control 26 of the treatment laser 1. The control unit 4 may be switched such that the control 26 with a prevailing signal of the analysis unit 24 automatically switches on the treatment laser 1 or else a release for the manual control of the treatment laser is effected, this control being made by the operating surgeon. In this manner it may be reliably prevented that the treatment laser 1 is for example unintentionally triggered when only healthy tissue has been diagnosed. Only with a minimum content of malignant tissue which is predetermined by setting the threshold value can the triggering of the treatment laser be effected, or this is effected automatically.

The monitor representation is effected continually with a repeating frequency of 50 Hz or more, nevertheless the inquiring frequency of the picture memory may be noticeably lower, for example three times per second. In this way there remains sufficient time in order to assemble the picture element data, arriving staggered with respect to time, to a complete picture and to numerically process this data. Moreover the monitor representation is not inhibited by the time windowing for the auto-focus, however in this time the treatment laser is blocked.

Figure 3:
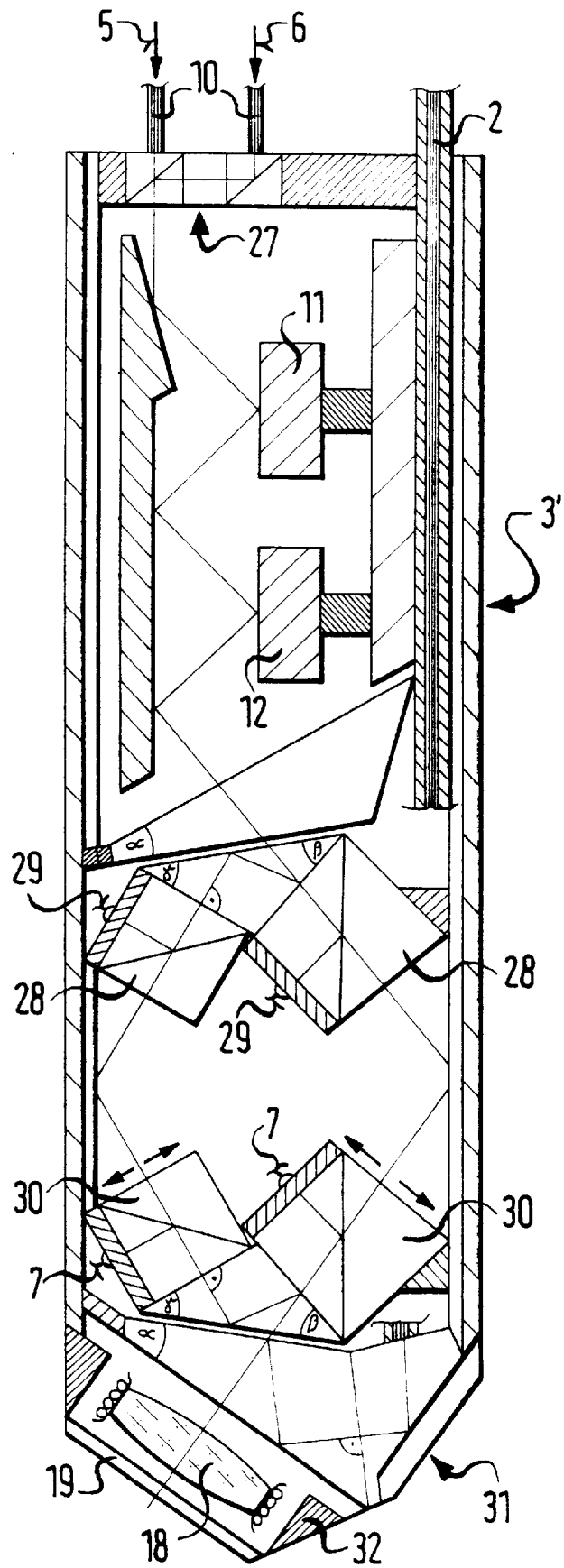
FIG. 3 shows another embodiment of the distal end section in longitudinal section.

The embodiment represented in FIG. 3 differs from that previously described in that the beams of the diagnosis lasers 5, 6 are led via separate monomode fibres 10 up to the distal end section 3' where they are combined via a suitable prism arrangement 27. From there they are in turn led to a vertical and then to a horizontal scanner 12, 11 respectively. From here a wavelength dependent beam splitting is effected by way of a corresponding prism arrangement. In beam splitter blocks 28 via photodiodes 29 the intensity of the light emitted from the diagnosis lasers 5, 6 is measured. By way of this acquisition of the irradiating diagnosis power in the control unit 4, intensity fluctuations of the diagnosis lasers 5, 6 may be compensated for, by which means a further possible source of errors may be removed. Via further beam splitting blocks 30, the beams then reach a prism arrangement 31 in which the beams of both diagnosis lasers 5, 6 are again unified and coupled to the beam path of the treatment laser 1 which likewise is connected to the distal end section 3'. The common beam path of the diagnosis lasers 5, 6 and the treatment laser 1 lead through the lens 18 which in this embodiment is set obliquely to the longitudinal axis of the distal end section 3', to a likewise obliquely set distal window 19. With this embodiment too the lens is part of the auto-focusing means, is provided with a coil arrangement on its outer circumference and is displaceably mounted in the axial direction. The permanent ring magnet which cooperates with the coil arrangement is designated with the reference numeral 32 in FIG. 3.

In comparison to the embodiment according to FIG. 2, with the embodiment according to FIG. 3 the photodiodes 7 for acquiring the intensity of the remitted light are arranged within the distal end section 3', these being at the base of the beam splitting blocks 30. Since here the intensity measurement is effected before passing the scanners 11, 12, the measurement is made considerably more simple since, on the one hand, the intensity of the reflected light is still markedly higher and, on the other hand, due to the measurement over the whole surface, a considerably larger quantity of light is available for the measurement. In so far as this is concerned this arrangement is to be preferred over that represented by way of FIG. 2.

Figure 4:
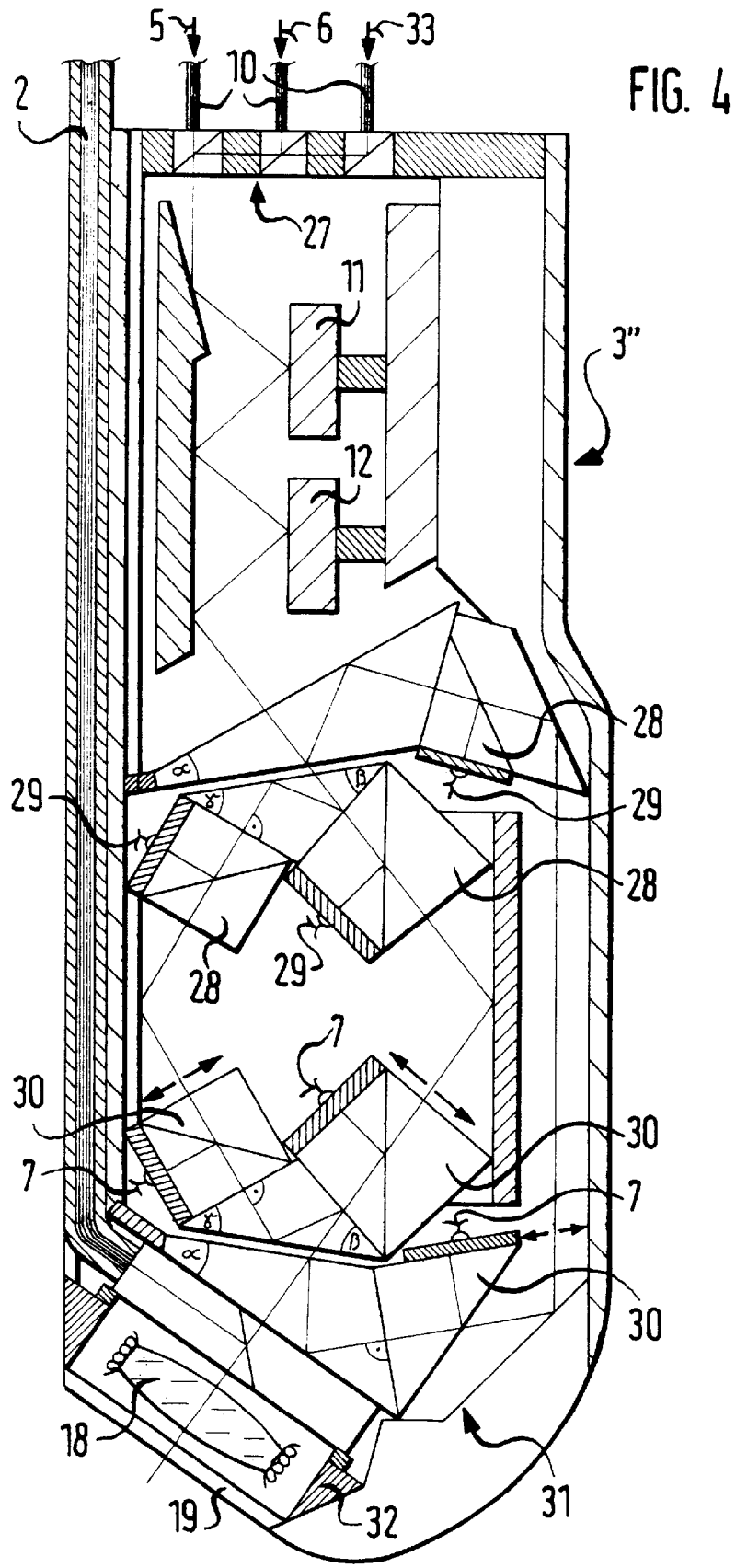
FIG. 4 shows a further embodiment in a view as in FIG. 3.

Also with the third embodiment described by way of FIG. 4 the photodiodes 7 are located within the distal end section 3". The construction of the distal end section 3" corresponds essentially to that represented by way of FIG. 3, which is why it is not described in detail here. The construction can be understood by way of the same reference numerals which are used. The angles α, β and γ are here chosen as follows:

α approximately 22.5°

β approximately 3375°

γ approximately 45°

The angles α and β agree with those of the embodiment according to FIG. 3.

The essential difference to the embodiment previously described lies in the fact that there are provided three diagnosis lasers 5, 6, and 33. The wavelengths of these three diagnosis lasers are so chosen that one laser functions in the red region, one laser in the green region and one in the blue region so that the beams add to natural white light. The prism arrangements are correspondingly modified and there are three photodiodes 29 for acquiring power fluctuations of the diagnosis laser and three photodiodes 7 for wavelength dependent intensity evaluation. The control unit 4 is correspondingly adapted, wherein apart from a further analog to digital converter there is also provided a further picture memory so that by inquiring three picture memories a natural color picture may be selectively represented on the monitor 23 in place of the numerically linked picture. This has the particular advantage that the treating surgeon independently of the numerically evaluated diagnosis result may also make a natural picture of the tissue location to be diagnosed, in other words of the diagnosis field irradiated by the diagnosis lasers.

We claim:

1. A device for endoscopic diagnosis and treatment of tissue, comprising:

a treatment laser having an optical axis;

at least one diagnosis laser for producing light beams of differing wavelengths;

receiving means for receiving the diagnosis laser light beams;

control and evaluation means for evaluating the diagnosis laser light and controlling the treatment laser; and a distal end member having a distal end in a vicinity of which the light beams exit and light guided to the receiving means enters, the receiving means being arranged in the distal end member.

2. A device according to claim 1, wherein at least two diagnosis lasers of differing wavelengths are provided, a separate receiving means being arranged in the distal end member for each of the diagnosis lasers.

3. A device according to claim 2, and further comprising horizontal and vertical scanning means arranged in the distal end member, the lasers being arranged to have beam paths that correspond and then impinge upon the scanning means.

4. A device according to claim 3, wherein the receiving means are operative to selectively acquire the light reflected from an irradiated location in one wavelength, which wavelength corresponds to that of the respective diagnosis laser.

5. A device according to claim 4, wherein the receiving means are arranged in the distal end member between the distal end and the scanning means.

6. A device according to claim 3, wherein each receiving means includes a photodiode which acquires an intensity of impinging light and outputs a corresponding signal, the control and evaluation means being operative for determining a matrix indicating a picture for a respective wavelength by a temporal course of the signal at the respective photodiodes and respective positions of the scanning means, the control and evaluation means being further operative to evaluate the matrices of different wavelengths and selectively release and activate the treatment laser based upon the matrices.

7. A device according to claim 1, and further comprising means for guiding light to the receiving means without using optical wave guides.

8. A device according to claim 1, wherein the diagnosis laser has an optical axis and is arranged so that the optical axis of the diagnosis laser corresponds with the optical axis of the treatment laser at least at the distal end of the distal end member.

9. A device according to claim 1, wherein three diagnosis lasers of differing wavelengths are provided.

10. A device according to claim 9, wherein the three diagnosis lasers are respectively of red, green and blue wavelength regions.

11. A device according to claim 1, and further comprising an auto-focusing device arranged in the distal end member and having a beam path that coincides with the diagnosis laser beam path as well as the treatment laser beam path at least at the distal end of the distal end member.

12. A device according to claim 11, wherein the distal end member includes a closing window, the auto-focusing device including a lens mounted in the closing window so as to be displaceable in a direction of the optical axis so as to permit focusing.

13. A device according to claim 11, wherein the auto-focusing device includes at least one photodiodes.

14. A device according to claim 11, wherein the receiving means is configured to form part of the auto-focusing device.

15. A device for endoscopic diagnosis and treatment of tissue, comprising:

a treatment laser having an optical axis;

at least two diagnosis lasers of differing wavelengths;

at least two receiving means for receiving the diagnosis laser light beams, each of the receiving means being arranged to receive light beams from a respective one of the diagnosis lasers, the receiving means being operative to selectively acquire light reflected from an irradiated location in one wavelength which corresponds to that of the respective diagnosis laser;

control and evaluation means for evaluating the diagnosis laser light and controlling the treatment laser;

a distal end member having a distal end in a vicinity of which the light beams exit and light guided to the receiving means enters, the receiving means being arranged in the distal end member; and means for guiding light to the receiving means without using optical wave guides.

* * * * *